(12) United States Patent
Quintela Fernández et al.

(10) Patent No.: US 10,376,529 B2
(45) Date of Patent: Aug. 13, 2019

(54) COMBINATION OF PENTACYCLIC TRITERPENES AND HYDROXYTYROSOL AND DERIVATIVES THEREOF

(71) Applicant: NATAC BIOTECH, S.L, Madrid (ES)

(72) Inventors: José Carlos Quintela Fernández, Madrid (ES); Esther De La Fuente García, Madrid (ES); Marco Pugliese, Sant Pere de Ribes (ES); Pilar Mancera Aroca, Roda de Barà (ES); Javier Bustos Santafé, Barcelona (ES); Juan Francisco Espinosa Parrilla, Badalona (ES); Noemí Virgili Treserres, Roda de Barà (ES); Blanca Wappenhans Battestini, Barcelona (ES)

(73) Assignee: NATAC BIOTECH, S.L., Madrid (ES)

( * ) Notice: Subject to any disclaimer, the term of this patent is extended or adjusted under 35 U.S.C. 154(b) by 129 days.

(21) Appl. No.: 14/897,948

(22) PCT Filed: Jun. 12, 2014

(86) PCT No.: PCT/EP2014/062269
§ 371 (c)(1),
(2) Date: Dec. 11, 2015

(87) PCT Pub. No.: WO2014/198842
PCT Pub. Date: Dec. 18, 2014

(65) Prior Publication Data
US 2016/0143930 A1    May 26, 2016

(30) Foreign Application Priority Data

Jun. 13, 2013  (EP) .................................... 13171906

(51) Int. Cl.
| | | |
|---|---|---|
| *A61K 31/7034* | (2006.01) | |
| *A61K 31/05* | (2006.01) | |
| *A61K 31/19* | (2006.01) | |
| *A61K 31/191* | (2006.01) | |
| *A61K 31/7048* | (2006.01) | |
| *A61K 9/00* | (2006.01) | |
| *A61K 31/047* | (2006.01) | |
| *A61K 31/085* | (2006.01) | |
| *A23L 33/10* | (2016.01) | |

(52) U.S. Cl.
CPC .......... *A61K 31/7034* (2013.01); *A23L 33/10* (2016.08); *A61K 9/0053* (2013.01); *A61K 31/047* (2013.01); *A61K 31/05* (2013.01); *A61K 31/085* (2013.01); *A61K 31/19* (2013.01); *A61K 31/191* (2013.01); *A61K 31/7048* (2013.01)

(58) Field of Classification Search
CPC ......... A23L 33/10; A61K 31/05; A61K 31/19; A61K 31/191; A61K 31/7034; A61K 31/7048; A61K 31/047; A61K 31/085; A61K 2300/00; A61K 9/0053
See application file for complete search history.

(56) References Cited

U.S. PATENT DOCUMENTS

| 6,037,492 A | 3/2000 | Lopez De Hierro et al. |
|---|---|---|
| 8,841,264 B2 * | 9/2014 | Raederstorff .......... A61K 31/05 514/32 |
| 2003/0236202 A1 | 12/2003 | Geelings et al. |

(Continued)

FOREIGN PATENT DOCUMENTS

| DE | 102006062566 A1 | 7/2008 |
|---|---|---|
| EP | 1230926 A | 8/2002 |

(Continued)

OTHER PUBLICATIONS

Chinese Office Action, dated Jun. 22, 2017, PRP 2014/80042906.8, NATAC Biotech, S. L.

(Continued)

*Primary Examiner* — Lawrence E Crane
(74) *Attorney, Agent, or Firm* — Tristan A. Fuierer; Olive Law Group, PLLC

(57) ABSTRACT

The present invention is related to a product comprising a pentacyclic triterpene of formula (I) and a hydroxytyrosol or derivatives thereof of formula (II), pharmaceutical compositions thereof and their uses as antioxidants, anti-inflammatories and neuron protectors.

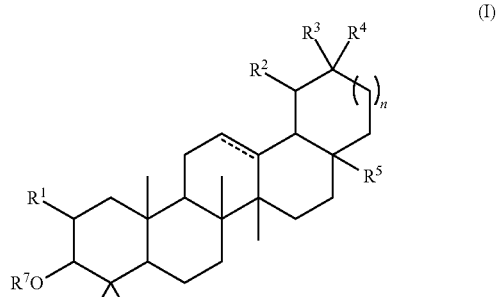

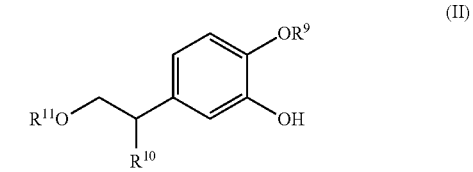

5 Claims, 2 Drawing Sheets

(56) References Cited

U.S. PATENT DOCUMENTS

| | | |
|---|---|---|
| 2009/0324801 A1 | 12/2009 | Lopez De Hierro et al. |
| 2010/0055163 A1 | 3/2010 | Garcia-Granados et al. |
| 2010/0056463 A1 | 3/2010 | Raederstorff et al. |
| 2010/0130621 A1 | 5/2010 | Raederstorff et al. |
| 2011/0054025 A1 | 3/2011 | Nieto Callejo et al. |

FOREIGN PATENT DOCUMENTS

| | | |
|---|---|---|
| EP | 1994835 A1 | 11/2008 |
| EP | 2033620 A1 | 3/2009 |
| EP | 2260851 A1 | 12/2010 |
| JP | 2001181198 A | 7/2001 |
| WO | 9804331 A1 | 2/1998 |
| WO | 03082259 A1 | 10/2003 |
| WO | 2006114467 A1 | 11/2006 |
| WO | 2007096446 A1 | 8/2007 |
| WO | 2008102047 A1 | 8/2008 |
| WO | 2011015692 A2 | 2/2011 |
| WO | 2013007850 A1 | 1/2013 |

OTHER PUBLICATIONS

Yuan, et al., "Effects of oleanic acid on apoptosis of PC12 cells induced by ABeta25-35," China Journal of Modern Medicine, 2013, pp. 33-37, vol. 23.

Liu et al., "Research progress pharmacological actions of hydroxytyrosol," Journal of Guangdong Pharmaceutical University, 2012, pp. 684-688, vol. 28.

Sheng G.Q. et al., "Protective effect of verbascoside on 1-methyl-4-phenylpyridinium ion-induced neurotoxicity in PC12 cells," Eur J Pharmacol, 2002, 451, 119-124.

Bianchi G., "Lipids and phenols in table olives," Eur J Lipid Sci Technol, 2003, 105, 229-242.

Koo KA., "Acteoside and its aglycones protect primary cultures of rat cortical cells from flutamate-induced excitotoxicity," Life Sci., 2006, 79, 709-716.

Liu, L., et al., "Solubility of Oleanolic Acid in Various Solvents from (288.3 to 328.3) K," Journal of Chemical and Engineering Data, 2007, 52, 2527-2528.

Rodríguez et al., "Antioxidant activity of effluents during the purification of hydroxytrosol and 3,4-dihydroxyphenyl glycol from olive oil waste," Eur Food Res Technol, 2007, 224, 733-741.

Fernández-Bolaños et al., "Hydroxytyrosol and Derivatives: Isolation, Synthesis, and Biological Properties," Current Organic Chemistry, 2008, 12, 442-463.

González-Correa JA., "Neuroprotective effect of hydroxytryosol and hydroxytyrosol acetate in rat brain slices subjected to hypoxia-reoxygenation," Neurosci Lett., 2008, 446, 143-146.

Cho SO., "Aralia cordata Protects Against Amyloid Beta Protein (25-35)-Induced Neurotoxicity in Cultured Neurons and Has Antidementia Activities in Mice," J Pharmacol Sci., 2009, 111, 22-32.

Jäger, S. et al., "Pentacyclic Triterpene Distribution in Various Plants—Rich Sources for a New Group of Multi-Potent Plant Extracts," Molecules, 2009, 14, 2016-2031.

Zhang X., "Hydroxytyrosol inhibits pro-inflammatory cytokines, iNOS, and COX-2 expression in human monocytic cells," Naunyn Schmiedebergs Arch Pharmacol., 2009, 379, 581-586.

Wu et al., "Measurement of free hydroxytyrosol in microdialysates from blood and brain of anesthetized rats by liquid chromatography with fluorescence detection," Journal Chromatography A, 2009, 1216, 3501-3507.

Rodríguez et al., "3,4-Dihydroxyphenylglycol (DHPG): An Important Phenolic Compound Present in Natural Table Olives," J Agric Food Chem, 2009, 57, 6298-6304.

Esposito E., "Protective effect of verbascoside in activated C6 glioma cells: possible molecular mechanisms," Naunyn Schmiedebergs Arch Pharmacol., 2010, 381, 93-105.

Omar, SH, "Cardioprotective and neuroprotective roles of oleuropein in olive," Saudi Pharmaceutical Journal, 2010, 18, 111-121.

Qian V., "Maslinic acid, a natural triterpenoid compound from Olea europaea, protects cortical neurons against oxygen-glucose deprivation-induced injury," Eur J Pharmacol., 2011, 670, 148-153.

Tasset I., "Olive oil reduces oxidative damage in a 3-nitropropionic acid-induced Huntington's disease-like rat model," Nutr Neurosci., 2011, 14, 106-111.

Aisha, AFA., et al., "Syzygium aromaticum extracts as good source of betulinic acid and potential anti-breast cancer," Brazilian Journal of Pharmacognosy, 2012, 22, 335-343.

Fernández-Mar, MI., et al., "Bioactive compounds in wine: Resveratrol, hydroxytyrosol and melatonin: A review," Food Chemistry, 2012, 130, 797-813.

Wang HQ, "Upregulation of Heme Oxygenase-1 by Acteoside Through ERK and PI3 K/Akt Pathway Confer Neuroprotection Against Beta-Amyloid-Induced Neurotoxicity," Neurotox Res., 2012, 21, 368-378, Abstract Only.

Fernández-Bolaños, "Biological Properties of Hydroxytyrosol and Its Derivatives," Ed. Boskow Dimitrios, ISBN: 978-953-307-921-9. Chapter 20 , Olive OIl—Constituents, Quality, Health Properties and Bioconversions, D. Boskou (ed.), Feb. 2012.

Vertuani, S., "Activity and Stability Sudies of Verbascoside, a Novel Antioxidant, in Dermo-Cosmetic and Pharmaceutical Topical Formulations," Molecules, 2011, 16, 7068-7080.

Schaffer S., "Hydroxytyrosol-Rich Olive Mill Wastewater Extract Protects Brain Cells in Vitro and ex Vivo," J. Agricul. Food Chem., 2007, 55, 5043-5049.

Daccache A., "Oleuropein and derivatives from olives as Tau aggregation inhibitors," Neurochem Int., 2011, 58, 700-707.

Martín E., "Beneficial actions of oleanolic acid in an experimental model of multiple schlerosis: A potential therapeutic role," AcBiochem Pharmacol, 2010, 79, 198-208.

Tamburelli L., "Olive oil protects the brain from aging, Alzheimer's and Parkinson's disease," internet publication, Apr. 9, 2013 (XP-002714047).

International Search Report, dated Sep. 3, 2014, PCT/EP2014/062269.

English Translation of Japanese Notice of Rejection, dated Jan. 9, 2018.

López-Miranda, J., et al.; Olive Oil and health: Summary of the II international conference on olive oil and healthconsensus report, Jaén and Córdoba (Spain) 2008; Nutrition, Metabolism & Cardiovascular Disease, 2010, pp. 284-294, vol. 20.

Lou-Bonafonte, José M., et al.; "Efficacy of bioactive compounds from extra virgin olive oil to modulate atherosclerosis development," Mol. Nutr. Food Res., 2012, pp. 1043-1057, vol. 56.

El, Sedef N., et al.; "Olive tree (Olea europaea) leaves: potential beneficial effects on human health," Nutrition Reviews, 2009, pp. 632-638, vol. 67.

* cited by examiner

COMBINATION OF PENTACYCLIC TRITERPENES AND HYDROXYTYROSOL AND DERIVATIVES THEREOF

CROSS-REFERENCE TO RELATED APPLICATIONS

This application is filed under the provisions of 35 U.S.C. § 371 and claims the priority of International Patent Application No. PCT/EP2014/062269 filed on 12 Jun 2014 entitled "COMBINATION OF PENTACYCLIC TRITERPENES AND HYDROXYTYROSOL AND DERIVATIVES THEREOF" in the name of José Carlos QUINTELA FERNÁNDEZ et al., which claims priority to European Patent Application No. 13171906.4 filed on 13 Jun 2013, both of which are hereby incorporated by reference herein in their entirety.

FIELD OF THE INVENTION

The present invention relates to a product comprising a pentacyclic triterpene and hydroxytyrosol or derivatives thereof, uses, pharmaceutical composition and kits thereof.

BACKGROUND OF THE INVENTION

Hydroxytyrosol is a plant secondary metabolite which can be found almost exclusively in leaves and fruit of olive (*Olea europaea* L.). It is especially abundant in olive mill wastewaters [Fernández-Bolaños, *Olive Oil—Constituents, quality, health properties and bioconversions*. Ed. Boskow Dimitrios, ISBN: 978-953-307-921-9. Chapter 20]. Hydroxytyrosol has been reported to be present in grapes (*Vitis vinifera* L.), although in a smaller proportion [Fernández, M I., et al., "Bioactive compounds in wine: Resveratrol, hydroxytyrosol and melatonin: A review", *Food Chemistry*, 130 (2012), pp. 797-813].

Hydroxytyrosol is a phenyl ethyl alcohol, 2-(3,4-dihydroxyphenyl)ethanol. It is a metabolite of oleuropein (ester of hydroxytyrosol, elenolic acid and glucose), from which it can be obtained by hydrolysis [Omar, S H., "Cardioprotective and neuroprotective roles of oleuropein in olive", *Saudi Pharmaceutical Journal*, 18 (2010), pp. 111-121].

Hydroxytyrosol's derivatives include tyrosol, oleuropein, verbascoside and related compounds derived from simple phenolic acids, such us gallic acid and others. Notable examples of verbascoside related compounds are those belonging to the phenylpropanoid glycoside group which are structurally characterized by the presence of caffeic acid moieties and 2-(3,4-dihydroxyphenyl)ethanol (hydroxytyrosol) moieties bound to a β-(D)-glucopyranoside [Vertuani, S., "Activity and Stability Studies of Verbascoside, A Novel Antoxidant, in Dermo-Cosmetic and Pharmaceutical Topical Formulations", *Molecules*, 16 (2011), pp. 7068-7080]. Due to its chemical structure, verbascoside (also known as acteoside) is highly soluble in hydrophilic solutions, such as methanol or hydroalcoholic mixtures. Verbascoside related compounds include echinacoside, martynoside, leucosceptoside, and other related phenylpropanoids.

Verbascoside is a secondary metabolite in plants and verbascoside related compounds are widely distributed in nature. Main sources include black horehound (*Ballota nigra* L.), pale purple cone-flower (*Echinacea pallida* (NUTT.)), devil's claw (*Harpagophytum procumbens* (BURCH)), bitter melon (*Momordica charantia* L.), olive (*Olea europaea* subsp. *Europaea*), figworts (*Scrophularia scorodonia* L.), Baikal skullcap (*Scutellaria baicalensis* (GEORGI)), sesame (*Sesamum indicum* L.) and common mullein (*Verbascum thapsus* L.) [Source Dr. Duke's Phytochemical and Etnobotanical Database]. Thus, verbascoside related compounds may be either chemically synthesized or obtained from the corresponding plant extracts.

Pentacyclic triterpenes are secondary plant metabolites widespread in plants, mainly in peel, leaves and stem bark. They are part of the chemical family of triterpenoids, polycyclic structures of thirty atoms of carbon. Triterpenoids are mainly subdivided in three families depending on their skeletal structures: lupane, oleane and ursane (see Table 1 below). In virtue of their structure, pentacyclic triterpenoids present very low solubility in hydrophilic solvents such as water. In the other hand, their solubility in organic solvents such us acetone or methanol has been demonstrated to be moderate-to-high [Liu, L., et al., "Solubility of Oleanolic Acid in Various Solvents from (288.3 to 328.3) K", *Journal of Chemical and Engineering Data*, 52 (2007), pp. 2527-2528].

Pentacyclic triterpenes are widely distributed in nature. Oleanolic acid is present in olive leaves (*Olea europaea* L.), marigold flowers (*Calendula officinalis* L.), rosemary leaves (*Rosmarinus officinalis* L.) and clove flowers (*Syzygium aromaticum* L.); maslinic acid is present in bearberry leaves (*Arctostaphylos uva-ursi* L.) and olive fruit (O/ea *europaea* L.); betulin is present in birch bark (*Betula alba* L.); betulinic acid is present in eucalyptus leaves (*Eucalyptus*), planes bark (*Platanus acerifolia*), rosemary leaves (*Rosmarinus officinalis* L.) [Jäger, S. et al., "Pentacyclic Triterpene Distribution in Various Plants—Rich sources for a New Group of Multi-Potent Plant Extracts", *Molecules*, 14 (2009), pp. 2016-2031] and clove leaves (*Syzygium aromaticum* L.) [Aisha, A F A., et al., "Syzigium *aromaticum* extracts as good source of betulinic acid and potential anti breast cancer", *Brazilian Journal of Pharmacognosy*, 22 (2012), pp. 335-343].

Hydroxytyrosol and related polyphenols are known as potent anti-oxidants and cytoprotectors. Different scientific articles and patents disclose their neuroprotective properties and its main target is believed to be related to mitochondrial targeting, one of the cell components mainly involved in neurodegenerative diseases [Schaffer S. "Hydroxytyrosol-rich olive wastewater extract protects brain cells in vitro and ex vivo" *J. Agricul. Food Chem.*, 55 (2007), pp. 5043-5049]. Among other studies, hydroxytyrosol and related phenols have been shown to protect neurons against hypoxia-reoxygenation [González-Correa JA. "Neuroprotective effect of hydroxytyrosol and hydroxytyrosol acetate in rat brain slices subjected to hypoxia-reoxygenation" *Neurosci Lett.*, 446 (2008), pp. 143-6.], act as Tau protein aggregation inhibitors in Alzheimer's disease [Daccache A. "Oleuropein and derivatives from olives as Tau aggregation inhibitors" *Neurochem Int.*, 58 (2011), pp. 700-7] or reducing oxidative damage in an animal model of Huntington disease [Tasset I. "Olive oil reduces oxidative damage in a 3-nitropropionic acid-induced Huntington's disease-like rat model" *Nutr Neurosci.*, 14 (2011), pp. 106-11]. Their use for neuroprotection has also been extensively described in different patents applications [US 2003/0236202A1, WO 2006/114467 A1, and US 2010/0130621 A1]. These derivatives have been also shown to exhibit anti-inflammatory effects that can mediate indirect neuroprotection [Zhang X. "Hydroxytyrosol inhibits pro-inflammatory cytokines, iNOS, and COX-2 expression in human monocytic cells" *Naunyn Schmiedebergs Arch Pharmacol.*, 379 (2009), pp. 581-6].

Verbascoside, which is mainly extracted from plants, also displays a neuroprotective profile, acting as anti-oxidant, cytoprotector and anti-inflammatory agent [Wang H Q. "Upregulation of heme oxygenase-1 by acteoside through ERK and PI3 K/Akt pathway confer neuroprotection against beta-amyloid-induced neurotoxicity" *Neurotox Res.*, 21 (2012), pp. 368-78; Koo K A. "Acteoside and its aglycones protect primary cultures of rat cortical cells from glutamate-induced excitotoxicity" *Life Sci.*, 79 (2006), pp. 709-16; Esposito E. "Protective effect of verbascoside in activated C6 glioma cells: possible molecular mechanisms" *Naunyn Schmiedebergs Arch Pharmacol.*, 381 (2010), pp. 93-105].

Triterpenic acids derived from plant extracts such as oleanolic acid or maslinic acid have been also extensively known for their neuroprotective and anti-neuroinflammatory properties [Martín E. "Beneficial actions of oleanolic acid in an experimental model of multiple sclerosis: A potential therapeutic role", *Biochem Pharmacol*, 79 (2010), pp. 198-208], primarily targeting neuronal apoptotic pathways and inhibiting neuroinflammatory signals such as microglial nitric oxide synthesis [Qian Y. "Maslinic acid, a natural triterpenoid compound from *Olea europaea*, protects cortical neurons against oxygen-glucose deprivation-induced injury" *Eur J Pharmacol.*, 670 (2011), pp. 148-53.; Cho S O. "*Aralia cordata* protects against amyloid beta protein (25-35)-induced neurotoxicity in cultured neurons and has anti-dementia activities in mice" *J Pharmacol Sci.*, 111 (2009), pp. 22-32]. These properties of triterpenoids or derivatives thereof have also been described in patent applications such as WO 2011/015692 A2.

Products comprising a combination of pentacyclic triterpenes and hydroxytyrosol or derivatives thereof have been disclosed, for example in WO 2007/096446 A1 and EP2 033 620 A1. Said applications disclose the use of said product combinations as a pronutrient in animal feed and for the preparation of a cream, respectively. However, these documents fail to disclose or suggest the use of such product combination for the protection of neurons and also fail to disclose a product comprising 3,4-dihydroxyphenylglycol.

As explained above, pentacyclic triterpenes, hydroxytyrosol or derivatives thereof have shown neuroprotective effectiveness when used individually. Surprisingly, the inventors have now discovered that the combination of specific pentacyclic triterpenes and hydroxytyrosol or specific derivatives thereof, such as verbascoside, can protect neurons in a more potent way than just the sum of the individual effects, i.e. the combination of specific pentacyclic triterpenes of formula (I) and hydroxytyrosol or specific derivatives thereof (having formula (II)), such as verbascoside, has a synergistic effect in the protection of neurons in particular when the weight of the compounds of formula (I) with respect to the weight of the compounds of formula (II) is in the range from 20:1 to 1:10.

SUMMARY OF THE INVENTION

In a first aspect, the present invention is directed to a product comprising:

a) one or more pentacyclic triterpene compounds of formula (I):

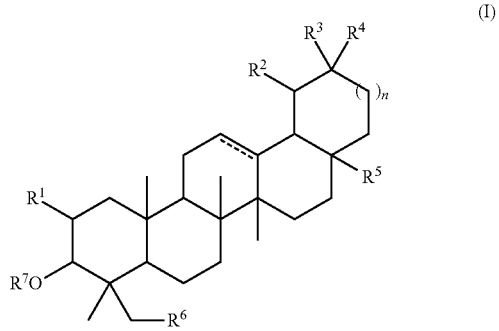

wherein $R^1$ is selected from the group consisting of H and OH;

$R^2$ is selected from the group consisting of H, methyl and propen-2-yl;

$R^3$ and $R^4$ are independently selected from the group consisting of H and methyl;

$R^5$ is selected from the group consisting of methyl, $CH_2OR^8$, $COOR^8$ and CHO;

$R^6$ is selected from the group consisting of H and $OR^8$;

$R^7$ and $R^8$ are independently selected from the group consisting of H and $C_1$-$C_3$ alkyl;

n is 0 or 1;

the dotted line represents a bond that may be present or not;

or a pharmaceutically acceptable salt or stereoisomer thereof; and b) one or more hydroxytyrosol derivative compounds of formula (II):

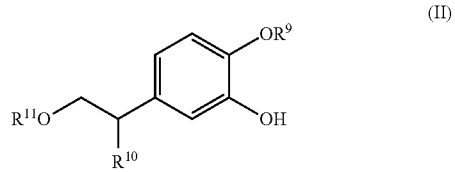

wherein $R^9$ is selected from the group consisting of H and $C_1$-$C_3$ alkyl;

$R^{10}$ is selected from the group consisting of H and OH;

$R^{11}$ is selected from the group consisting of H, $C_1$-$C_{17}$ alkylcarbonyl,

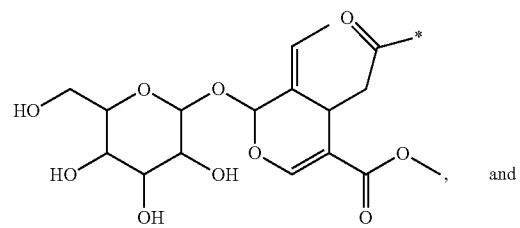

and

-continued

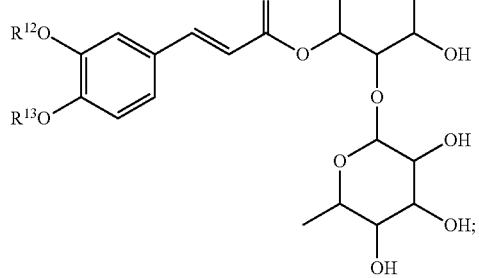

$R^{12}$ and $R^{13}$ are independently selected from the group consisting of H and $C_1$-$C_3$ alkyl;
$R^{14}$ is selected from the group consisting of H and

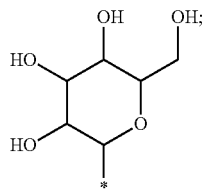

and
* represents the attachment point to the rest of the molecule;
or a pharmaceutically acceptable salt or stereoisomer thereof;
for use in the treatment and/or prevention of a disease selected from the group consisting of Creutzfeldt-Jakob disease, Alzheimer's disease, Huntington's disease, Lewy body disease, Parkinson's disease, Pick's disease, amyotrophic lateral sclerosis, neurofibromatosis, epilepsy, brain injury, stroke, multiple sclerosis, ischemic hypoxia, spinal cord injury, loss of memory, mild cognitive impairment, dementia, and multiple infarct dementia.

In a second aspect, the present invention relates to a product comprising:
a) one or more compounds of formula (I)

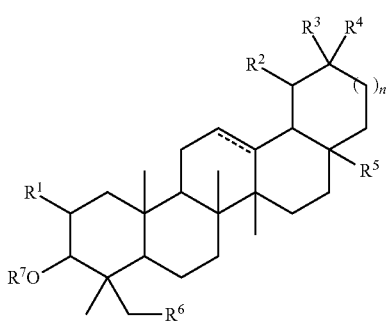

wherein
$R^1$ is selected from the group consisting of H and OH;
$R^2$ is selected from the group consisting of H, methyl and propen-2-yl;
$R^3$ and $R^4$ are independently selected from the group consisting of H and methyl;

$R^5$ is selected from the group consisting of methyl, $CH_2OR^8$, $COOR^8$ and CHO;
$R^6$ is selected from the group consisting of H and $OR^8$;
$R^7$ and $R^8$ are independently selected from the group consisting of H and $C_1$-$C_3$ alkyl;
n is 0 or 1;
the dotted line represents a bond that may be present or not;
or a pharmaceutically acceptable salt or stereoisomer thereof; and
b) one or more compounds of formula (II)

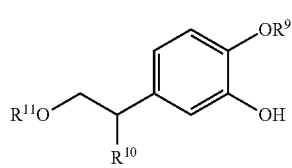

wherein
$R^9$ is selected from the group consisting of H and $C_1$-$C_3$ alkyl;
$R^{10}$ is selected from the group consisting of H and OH;
$R^{11}$ is selected from the group consisting of H, $C_1$-$C_{17}$ alkylcarbonyl,

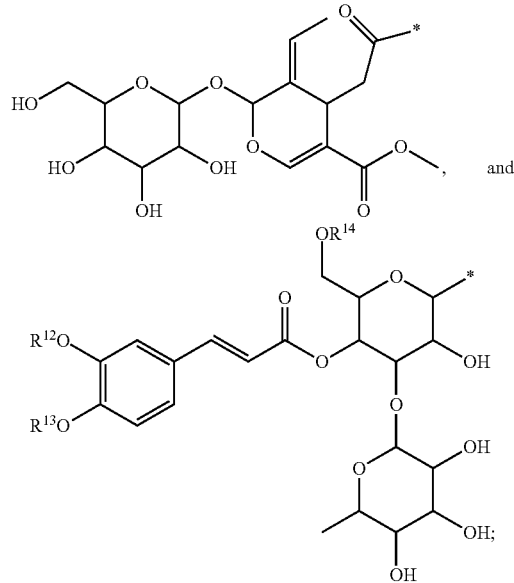

$R^{12}$ and $R^{13}$ are independently selected from the group consisting of H and $C_1$-$C_3$ alkyl;
$R^{14}$ is selected from the group consisting of H and

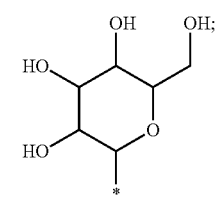

and
* represents the attachment point to the rest of the molecule;
or a pharmaceutically acceptable salt or stereoisomer thereof;
with the proviso that the product comprises a compound of formula (II) wherein $R^9$ and $R^{11}$ are H, and $R^{10}$ is OH, i.e. 3,4-dihydroxyphenylglycol.

In a third aspect, the present invention relates to a pharmaceutical composition comprising the product defined in the second aspect and a pharmaceutically acceptable excipient.

In a fourth aspect, the present invention relates to a product as defined in the second aspect for use as a medicament.

In a fifth aspect, the present invention relates to a functional food comprising a product as defined in the second aspect.

In a sixth aspect, the present invention relates to the use of a product as defined in the second aspect for the manufacture of a functional food.

DESCRIPTION OF THE INVENTION

Figure 1:
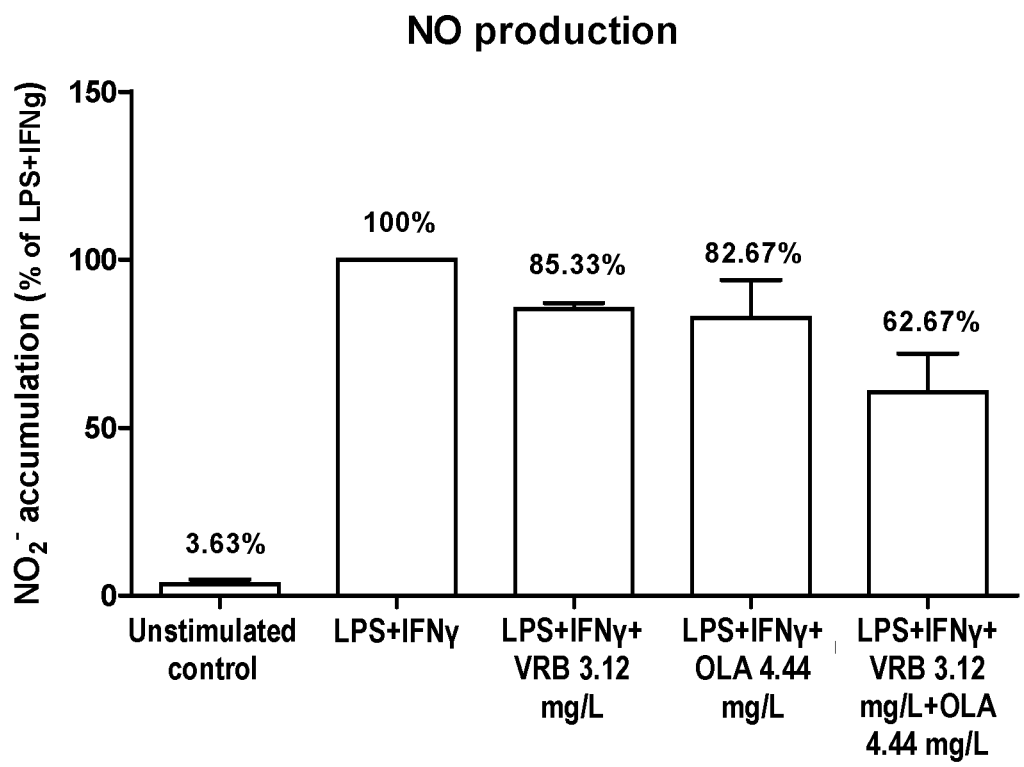
FIG. 1 shows NO production analysis in Lipopolysaccharide (LPS) plus gamma Interferon (IFNg) stimulated BV2 microglia treated with verbascoside (VRB) 3.12 mg/L, oleanolic acid (OLA) 4.44 mg/L or the combination of both. Results expressed as mean+SEM.

The term "alkyl" as employed herein alone or as part of another group designates a linear or branched saturated monovalent hydrocarbon chain containing from one to seventeen, preferably from one to thirteen, more preferably from one to ten, even more preferably from 1 to 8 and most preferably from one to three carbon atoms. Examples of alkyls are methyl, ethyl, propyl, and 2-propyl.

The term "alkylcarbonyl" as employed herein alone or as part of another group designates an alkyl group as defined above linked to a carbonyl —(C=O)— group. When the number of carbons of an alkylcarbonyl group is specified it is to be understood that the specified number of carbons do not include the carbon in the carbonyl group (i.e. $C_4$-alkylcarbonyl is, for example, a $CH_3$—$(CH_2)_3$—C(=O)— group). Examples of alkylcarbonyl groups are acetyl, propionyl, butiryl, oleyl, stearyl and palmitoyl.

As used herein, the term "pharmaceutically acceptable salt" embraces salts with a pharmaceutically acceptable base, which are synthesized from the parent compound which contains an acidic moiety by addition of a pharmaceutically acceptable base. Pharmaceutically acceptable bases include alkali metal (e.g., sodium or potassium) and alkali earth metal (e.g., calcium or magnesium) hydroxides and organic bases, such as alkyl amines, arylalkyl amines, and heterocyclic amines. For instance, pharmaceutically acceptable salts of compounds provided herein are synthesized from the parent compound which contains an acid moiety by conventional chemical methods. Generally, such salts are, for example, prepared by reacting the free base or free acid forms of these compounds with a stoichiometric amount of the appropriate acid or base, respectively, in water or in an organic solvent or in a mixture of the two.

All stereoisomers of the compounds of this invention are contemplated either alone or as mixtures thereof. The process of preparation can utilize racemates, enantiomers, or diastereomers as starting materials. When diastereomeric or enantiomeric products are prepared, they can be separated by conventional methods, for example, chromatographic or functional crystallization.

The present invention relates to new medical uses of a product that comprises one or more compounds of formula (I) and one or more compounds of formula (II) as defined in the first aspect, but also to a novel product which comprises a compound of formula (I) and one or more compounds of formula (II) as defined in the second aspect.

Compounds of formula (I) and compounds of formula (II) have been described in the prior art as having a neuroprotective profile, acting as anti-oxidants, cytoprotectors and/or anti-inflammatory agents. This neuroprotective effect has been described for the compounds of formula (I) and of formula (II) individually. Surprisingly, the inventors have now discovered that the combination of a compound of formula (I) and a compound of formula (II), as defined above, shows a synergistic effect as neuroprotector, i.e. the combination of the compound of formula (I) and the compound of formula (II) can protect neurons in a more potent way than just the sum of the individual effects. Thus, the combination of a compound of formula (I) and a compound of formula (II) may be used in the treatment and/or prevention of neurodegenerative diseases and diseases related to neuronal damage.

In the first aspect, the present invention relates to the product according to the present invention which comprises:
a) one or more pentacyclic triterpene compounds of formula (I):

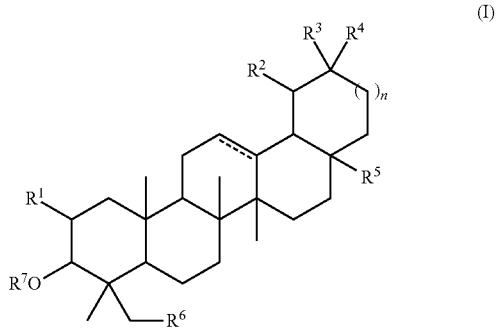

wherein
$R^1$ is selected from the group consisting of H and OH;
$R^2$ is selected from the group consisting of H, methyl and propen-2-yl;
$R^3$ and $R^4$ are independently selected from the group consisting of H and methyl;
$R^5$ is selected from the group consisting of methyl, $CH_2OR^8$, $COOR^8$ and CHO;
$R^6$ is selected from the group consisting of H and $OR^8$;
$R^7$ and $R^8$ are independently selected from the group consisting of H and $C_1$-$C_3$ alkyl;

n is 0 or 1;
the dotted line represents a bond that may be present or not;
or a pharmaceutically acceptable salt or stereoisomer thereof; and b) one or more hydroxytyrosol derivative compounds of formula (II):

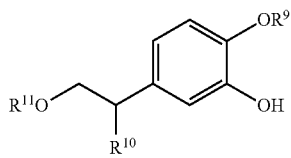

(II)

wherein
$R^9$ is selected from the group consisting of H and $C_1$-$C_3$ alkyl;
$R^{10}$ is selected from the group consisting of H and OH;
$R^{11}$ is selected from the group consisting of H, $C_1$-$C_{17}$ alkylcarbonyl,

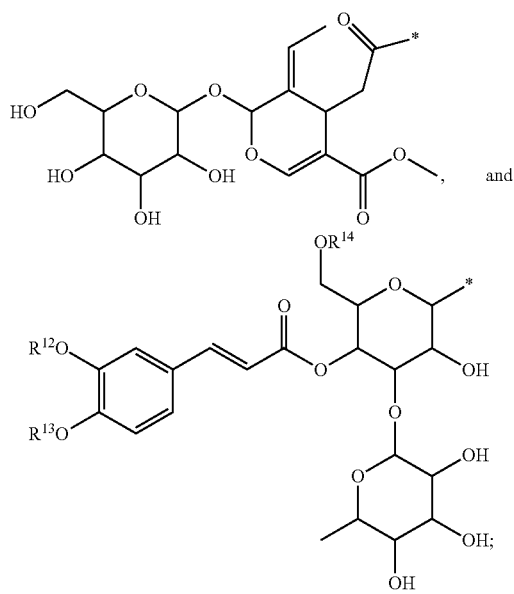

$R^{12}$ and $R^{13}$ are independently selected from the group consisting of H and $C_1$-$C_3$ alkyl;
$R^{14}$ is selected from the group consisting of H and

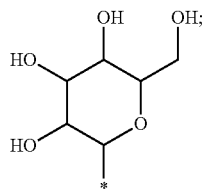

and
* represents the attachment point to the rest of the molecule;
or a pharmaceutically acceptable salt or stereoisomer thereof;

for use in the treatment and/or prevention of a disease selected from the group consisting of Creutzfeldt-Jakob disease, Alzheimer's disease, Huntington's disease, Lewy body disease, Parkinson's disease, Pick's disease, amyotrophic lateral sclerosis, neurofibromatosis, epilepsy, brain injury, stroke, multiple sclerosis, ischemic hypoxia, spinal cord injury, loss of memory, mild cognitive impairment, dementia, and multiple infarct dementia.

The expression "one or more" refers to 1, 2, 3, 4, 5, 6, 7, 8, 9 or 10 compounds; preferably 1, 2, 3, 4 or 5 compounds; more preferably 1, 2 or 3 compounds; even more preferably 1 or 2 compounds.

In a particular embodiment the product for use according to the present invention comprises one or more compounds of formula (I) wherein $R^2$ is H.

In another particular embodiment the product for use according to the present invention comprises one or more compounds of formula (I) wherein $R^3$ and $R^4$ are methyl.

In another particular embodiment the product for use according to the present invention comprises one or more compounds of formula (I) wherein $R^5$ is selected from the group consisting of methyl, $CH_2OH$, COOH; preferably COOH or $CH_2OH$, more preferably COOH.

In another particular embodiment the product for use according to the present invention comprises one or more compounds of formula (I) wherein $R^6$ is H.

In another particular embodiment the product for use according to the present invention comprises one or more compounds of formula (I) wherein $R^7$ and $R^8$ are independently selected from the group consisting of H and methyl, preferably $R^7$ and $R^8$ are H.

In another particular embodiment the product for use according to the present invention comprises one or more compounds of formula (I) wherein n is 0.

In another particular embodiment the product for use according to the present invention comprises the one or more compounds of formula (I) wherein the dotted line represents a bond that is present (i.e. forming a double bond).

In a preferred embodiment the product for use according to the present invention comprises one or more compounds of formula (I) selected from the group consisting of lupeol, betulin, betulinic acid, erythrodiol, oleanolic acid, maslinic acid, uvaol and ursolic acid; more preferably from the group consisting of erythrodiol, oleanolic acid, and maslinic acid; even more preferably from oleanolic acid, and maslinic acid.

In a particular embodiment the product for use according to the present invention comprises one or more compounds of formula (II) wherein $R^9$ is selected from H and methyl, preferably H.

In another particular embodiment the product for use according to the present invention comprises one or more compounds of formula (II) wherein $R^{11}$ is selected from the group consisting of H and

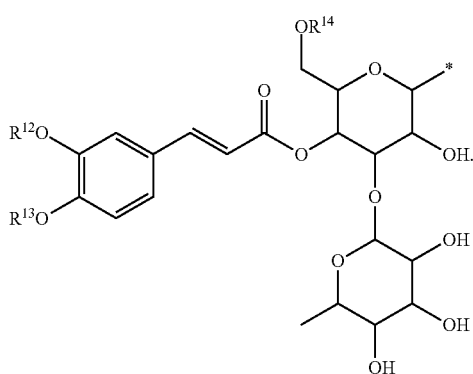

In another particular embodiment the product for use according to the present invention comprises one or more compounds of formula (II) wherein $R^{12}$ is selected from the group consisting of H and methyl, preferably H.

In another particular embodiment the product for use according to the present invention comprises one or more compounds of formula (II) wherein $R^{13}$ is selected from the group consisting of H and methyl, preferably H.

In another particular embodiment the product for use according to the present invention comprises one or more compounds of formula (II) wherein $R^{14}$ is H.

In a preferred embodiment the product for use according to the present invention comprises one or more compounds of formula (II) selected from the group consisting of hydroxytyrosol, verbascoside, oleuropein, 3,4-dihydroxyphenylglycol, echinacoside, martynoside, and leucoscepto-side (their chemical structures are provided below); preferably selected from hydroxytyrosol, verbascoside, 3,4-dihydroxyphenylglycol, and oleuropein; more preferably selected from the group consisting of hydroxytyrosol, verbascoside, and oleuropein; even more preferably selected from the group consisting of hydroxytyrosol, verbascoside, and 3,4-dihydroxyphenylglycol; still more preferably selected from the group consisting of hydroxytyrosol and verbascoside.

In one embodiment, the product for use according to the present invention comprises a combination of a compound of formula (I) and a compound of formula (II) selected from the group consisting of:
 oleanolic acid and verbascoside;
 maslinic acid and verbascoside;
 oleanolic acid and oleuropein; and
 oleanolic acid and hydroxytyrosol.

In one particular embodiment, the product for use according to the present invention comprises a combination of a compound of formula (I) and a compound of formula (II) selected from the group consisting of:
 oleanolic acid and verbascoside;
 maslinic acid and verbascoside; and
 oleanolic acid and hydroxytyrosol.

In another embodiment, in the product for use according to the present invention, the weight of the one or more compounds of formula (I) with respect to the weight of the one or more compound of formula (II) is in the range from 20:1 to 1:10, preferably from 10:1 to 1:10, more preferably from 10:1 to 1:1, still more preferably from 5:1 to 1:1.

In one particular embodiment, the product for use according to the present invention comprises:
 oleanolic acid and verbascoside, wherein the weight of the oleanolic acid with respect to the weight of the verbascoside is in the range from 10:1 to 1:1, preferably between 5:1 to 1:1, more preferably from 2:1 to 1:1;
 maslinic acid and verbascoside, wherein the weight of the maslinic acid with respect to the weight of the verbascoside is in the range from 10:1 to 1:1, preferably from 5:1 to 1:1, more preferably from 5:1 to 3:1;
 oleanolic acid and oleuropein, wherein the weight of the oleanolic acid with respect to the weight of the oleuropein is in the range from 10:1 to 1:1, preferably from 5:1 to 1:1; and
 oleanolic acid and hydroxytyrosol, wherein the weight of the oleanolic acid with respect to the weight of the hydroxytyrosol is in the range from 10:1 to 1:1, preferably from 5:1 to 1:1, more preferably from 4:1 to 2:1.

In another particular embodiment, the product for use according to the present invention comprises:
 oleanolic acid and verbascoside, wherein the weight of the oleanolic acid with respect to the weight of the verbascoside is in the range from 10:1 to 1:1, preferably between 5:1 to 1:1, more preferably from 2:1 to 1:1;
 maslinic acid and verbascoside, wherein the weight of the maslinic acid with respect to the weight of the verbascoside is in the range from 10:1 to 1:1, preferably from 5:1 to 1:1, more preferably from 5:1 to 3:1; and
 oleanolic acid and hydroxytyrosol, wherein the weight of the oleanolic acid with respect to the weight of the hydroxytyrosol is in the range from 10:1 to 1:1, preferably from 5:1 to 1:1, more preferably from 4:1 to 2:1.

The present invention also relates to the use of product which comprises one or more compounds of formula (I) and one or more compounds of formula (II) as defined above, for use in the manufacture of a medicament for the treatment and/or prevention of a disease selected from the group consisting of Creutzfeldt-Jakob disease, Alzheimer's disease, Huntington's disease, Lewy body disease, Parkinson's disease, Pick's disease, amyotrophic lateral sclerosis, neurofibromatosis, epilepsy, brain injury, stroke, multiple sclerosis, ischemic hypoxia, spinal cord injury, loss of memory, mild cognitive impairment, dementia, and multiple infarct dementia.

The invention also relates to a method of treatment and/or prevention of a subject in need thereof of a disease selected from the group consisting of Creutzfeldt-Jakob disease, Alzheimer's disease, Huntington's disease, Lewy body disease, Parkinson's disease, Pick's disease, amyotrophic lateral sclerosis, neurofibromatosis, epilepsy, brain injury, stroke, multiple sclerosis, ischemic hypoxia, spinal cord injury, loss of memory, mild cognitive impairment, dementia, and multiple infarct dementia, which comprises the administration of a therapeutically effective amount of a product which comprises one or more compounds of formula (I) and one or more compounds of formula (II) as defined above.

The terms "treating" and "treatment", as used herein, means reversing, alleviating, inhibiting the progress of, the disease or condition to which such term applies, or one or more symptoms of such disease or condition.

The terms "preventing" and "prevention", as used herein, means inhibiting the onset of the disease or condition to which this term applies, or one or more symptoms of such disease or condition.

The term "functional food", as used herein, means a food given an additional function related to health-promotion or disease prevention by adding to the food new ingredients. More specifically within the context of the present invention the functions added to the functional food are related to the treatment or prevention of a disease selected from the group consisting of Creutzfeldt-Jakob disease, Alzheimer's disease, Huntington's disease, Lewy body disease, Parkinson's disease, Pick's disease, amyotrophic lateral sclerosis, neurofibromatosis, epilepsy, brain injury, stroke, multiple sclerosis, ischemic hypoxia, spinal cord injury, loss of memory, mild cognitive impairment, dementia, and multiple infarct dementia.

In one embodiment the one or more compounds of formula (I) and the one or more compounds of formula (II), as defined above, are administered simultaneously, sequentially or separately. In said embodiment the product is designed to enable the simultaneous, sequential or separate administration of the compound of formula (I) and the compound of formula (II).

Simultaneous administration may, e.g., take place in the form of one composition comprising both the one or more compounds of formula (I) and the one or more compounds of formula (II), as defined above, or by simultaneously administering, i.e. administering at the same time, the one or more compounds of formula (I) and the one or more compounds of formula (II) which are formulated independently, i.e. not forming part of the same composition.

Sequential administration preferably means administration of one of the compound of formula (I) or the compound of formula (II) at one time point, and the other compound, i.e. the compound of formula (II) or the compound of formula (I), respectively at a different time point, that is, in a chronically staggered manner.

Separate administration preferably means administration of the one or more compounds of formula (I) and the one or more compounds of formula (II), as defined above, independently of each other at different time points.

When administered sequentially or separately, either the one or more compounds of formula (I) or the one or more compounds of formula (II) may be administered first. In one particular embodiment, the one or more compounds of formula (I) is administered first. In another particular embodiment, the one or more compounds of formula (II) is administered first.

In one embodiment the product for use according to the present invention comprises the one or more compounds of formula (I) and the one or more compounds of formula (II) forming part of the same composition for simultaneous administration.

In another embodiment, the product for use according to the present invention comprises the one or more compounds of formula (I) and the one or more compounds of formula (II) provided as separate compositions, preferably for simultaneous administration.

The compounds of formula (I) and the compound of formula (II) may be administered at different dosages depending on different factors such as the particular galenic formulation, the mode of application, and the particular disease or condition to be treated and/or prevented. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose. Preferred doses for the compounds of formula (I) are from 20 mg/day to 400 mg/day, more preferably from 20 mg/day to 200 mg/day, still more preferably from 50 mg/day to 150 mg/day, even more preferably from 75 mg/day to 100 mg/day. Preferred doses for the compounds of formula (II) are from 5 mg/day to 500 mg/day, more preferably from 50 mg/day to 250 mg/day, even more preferably from 100 mg/day to 200 mg/day.

Compounds of the invention may be administered by the oral, sublingual, parenteral, subcutaneous, intramuscular, intravenous, transdermal, intranasal, intraocular, and/or rectal routes.

In the second aspect, the present invention relates to a product comprising one or more compounds of formula (I) or pharmaceutically acceptable salt or stereoisomer thereof, and one or more compounds of formula (II) or pharmaceutically acceptable salt or stereoisomer thereof, as defined above, with the proviso that the product comprises a compound of formula (II) wherein $R^9$ and $R^{11}$ are H, and $R^{16}$ is OH (i.e. the product comprises 3,4-dihydroxyphenylglycol).

In a preferred embodiment, the product according to the second aspect comprises a) one or more compounds of formula (I) and b) one or more compounds of formula (II) in a weight ratio a)/b) not lower than 1; with the proviso that:
when the product comprises oleanolic acid (a compound of formula (I) wherein $R^1$, $R^2$, $R^6$, $R^7$ and $R^8$ are H, $R^3$ and $R^4$ are methyl, $R^5$ is $COOR^8$, n is 1, and the dotted line is present), and hydroxytyrosol (a compound of formula (II) wherein $R^9$-$R^{11}$ are H), then the weight of oleanolic acid is at least 3 times the weight of the hydroxytyrosol; and
when the product comprises hydroxytyrosol (a compound of formula (II) wherein $R^9$-$R^{11}$ are H), maslinic acid (a compound of formula (I) wherein $R^1$ is OH, $R^2$, $R^6$, $R^2$ and $R^8$ are H, $R^3$ and $R^4$ are methyl, $R^5$ is $COOR^8$, n is 1 and the dotted line is present), and oleanolic acid (a compound of formula (I) wherein $R^1$, $R^2$, $R^6$, $R^7$ and $R^8$ are H, $R^3$ and $R^4$ are methyl, $R^5$ is $COOR^8$, n is 1, and the dotted line is present) in a weight ratio maslinic acid/oleanolic acid greater than 1, then the weight of maslinic acid is at least 10 times the weight of hydroxytyrosol.

In a particular embodiment the product according to the present invention comprises one or more compounds of formula (I) wherein $R^2$ is H.

In another particular embodiment the product according to the present invention comprises one or more compounds of formula (I) wherein $R^3$ and $R^4$ are methyl.

In another particular embodiment the product according to the present invention comprises one or more compounds of formula (I) wherein $R^5$ is selected from the group consisting of methyl, $CH_2OH$, and COOH; preferably COOH or $CH_2OH$, more preferably COOH.

In another particular embodiment the product according to the present invention comprises one or more compounds of formula (I) wherein $R^6$ is H.

In another particular embodiment the product according to the present invention comprises one or more compounds of formula (I) wherein $R^7$ and $R^8$ are independently selected from the group consisting of H and methyl, preferably $R^7$ and $R^8$ are H.

In another particular embodiment the product according to the present invention comprises one or more compounds of formula (I) wherein n is 0.

In another particular embodiment the product according to the present invention comprises one or more compounds of formula (I) wherein the dotted line represents a bond that is present (i.e. forming a double bond).

In a preferred embodiment the product according to the present invention comprises one or more compounds of formula (I) selected from the group consisting of lupeol, betulin, betulinic acid, erythrodiol, oleanolic acid, maslinic acid, uveol, and ursolic acid (see Table 1); more preferably selected from the group consisting of erythrodiol, oleanolic acid, maslinic acid and mixtures thereof; even more preferably selected from oleanolic acid, and maslinic acid.

TABLE 1

| Triterpene family | Name | $R^{15}$ | $R^{16}$ |
|---|---|---|---|
| Lupane | Lupeol | $CH_3$ | — |
|  | Betulin | $CH_2OH$ | — |
|  | Betulinic acid | COOH | — |
| Oleane | Erythrodiol | $CH_2OH$ | H |
|  | Oleanolic acid | COOH | H |
|  | Maslinic acid | COOH | OH |
| Ursane | Uvaol | $CH_2OH$ | — |
|  | Ursolic acid | COOH | — |

As explained above, the present invention relates to a product comprising one or more compounds of formula (I) or pharmaceutically acceptable salts or stereoisomers thereof, and one or more compounds of formula (II) or pharmaceutically acceptable salts or stereoisomers thereof, as defined above.

In a particular embodiment, the product comprises a compound of formula (II) which is 3,4-dihydroxyphenyl-glycol and one or more additional compounds of formula (II) wherein $R^9$ is selected from H and methyl, preferably H.

In another particular embodiment, the product comprises a compound of formula (II) which is 3,4-dihydroxyphenyl-glycol and one or more additional compounds of formula (II) wherein $R^{11}$ is selected from the group consisting of H and

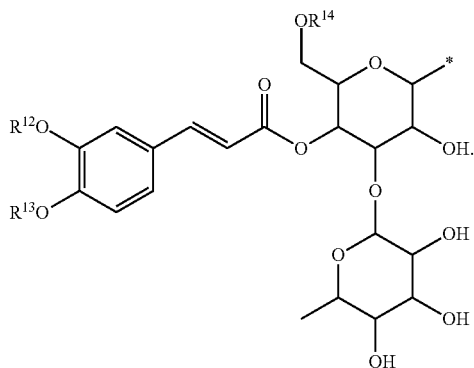

In another particular embodiment, the product comprises a compound of formula (II) which is 3,4-dihydroxyphenyl-glycol and one or more additional compounds of formula (II) wherein $R^{12}$ is selected from the group consisting of H and methyl, preferably H.

In another particular embodiment, the product comprises a compound of formula (II) which is 3,4-dihydroxyphenyl-glycol and one or more additional compounds of formula (II) wherein $R^{13}$ is selected from the group consisting of H and methyl, preferably H.

In another particular embodiment, the product comprises a compound of formula (II) which is 3,4-dihydroxyphenyl-glycol and one or more additional compounds of formula (II) wherein $R^{14}$ is H.

In a preferred embodiment, the product comprises a compound of formula (II) which is 3,4-dihydroxyphenyl-glycol and one or more additional compounds of formula (II) selected from hydroxytyrosol, verbascoside, oleuropein, echinacoside, martynoside, leucosceptoside, and mixtures thereof (their chemical structures are provided below); preferably one of the compounds of formula (II) is selected from hydroxytyrosol, verbascoside, oleuropein and mixtures thereof; more preferably one of the compounds of formula (II) is selected from hydroxytyrosol, verbascoside and mixtures thereof.

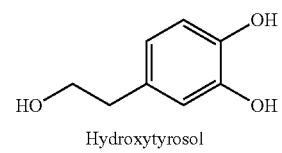

Hydroxytyrosol

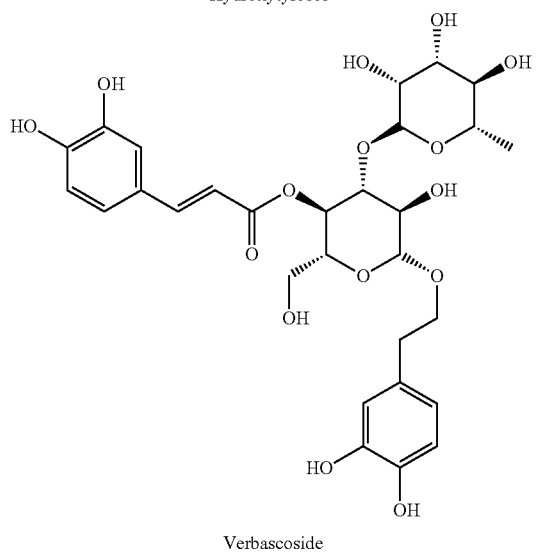

Verbascoside

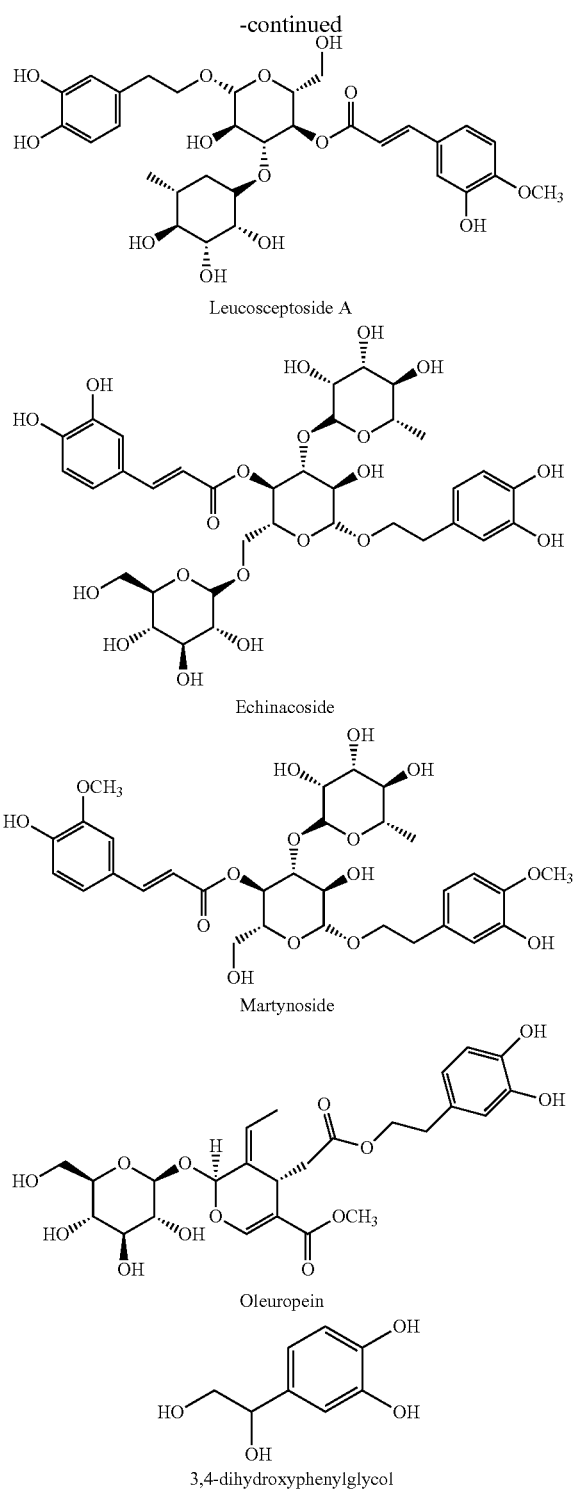

Leucosceptoside A

Echinacoside

Martynoside

Oleuropein 3,4-dihydroxyphenylglycol

In one embodiment, the product according to the present invention comprises a combination of a compound of formula (I) and compounds of formula (II) selected from the group consisting of:
- oleanolic acid, 3,4-dihydroxyphenylglycol and verbascoside;
- maslinic acid, 3,4-dihydroxyphenylglycol and verbascoside;
- oleanolic acid, 3,4-dihydroxyphenylglycol and oleuropein; and
- oleanolic acid, 3,4-dihydroxyphenylglycol and hydroxytyrosol.

In one particular embodiment, the product according to the present invention comprises a combination of a compound of formula (I) and compounds of formula (II) selected from the group consisting of:
- oleanolic acid, 3,4-dihydroxyphenylglycol and verbascoside;
- maslinic acid, 3,4-dihydroxyphenylglycol and verbascoside; and
- oleanolic acid, 3,4-dihydroxyphenylglycol and hydroxytyrosol.

In another embodiment, in the product according to the present invention, the weight of the compound(s) of formula (I) with respect to the weight of the compound(s) of formula (II) is in the range from 20:1 to 1:10, more preferably form 20:1 to 1:1, still more preferably from 10:1 to 1:1, even more preferably from 5:1 to 1:1.

In one particular embodiment, the product according to the present invention comprises:
- oleanolic acid, 3,4-dihydroxyphenylglycol and verbascoside, wherein the weight of the oleanolic acid with respect to the weight of the verbascoside is in the range from 10:1 to 1:1, preferably between 5:1 to 1:1, more preferably from 2:1 to 1:1;
- maslinic acid, 3,4-dihydroxyphenylglycol and verbascoside, wherein the weight of the maslinic acid with respect to the weight of the verbascoside is in the range from 10:1 to 1:1, preferably from 5:1 to 1:1, more preferably from 5:1 to 3:1;
- oleanolic acid, 3,4-dihydroxyphenylglycol and oleuropein, wherein the weight of the oleanolic acid with respect to the weight of the oleuropein is in the range from 10:1 to 1:1, preferably from 5:1 to 1:1; and
- oleanolic acid, 3,4-dihydroxyphenylglycol and hydroxytyrosol, wherein the weight of the oleanolic acid with respect to the weight of the hydroxytyrosol is in the range from 10:1 to 1:1, preferably from 5:1 to 1:1, more preferably from 4:1 to 2:1.

In one particular embodiment, the product according to the present invention comprises:
- oleanolic acid, 3,4-dihydroxyphenylglycol and verbascoside, wherein the weight of the oleanolic acid with respect to the weight of the verbascoside is in the range from 10:1 to 1.1:1, preferably between 5:1 to 1.1:1, more preferably from 2:1 to 1.1:1;
- maslinic acid, 3,4-dihydroxyphenylglycol and verbascoside, wherein the weight of the maslinic acid with respect to the weight of the verbascoside is in the range from 10:1 to 1.1:1, preferably from 5:1 to 1.1:1, more preferably from 5:1 to 3:1; and
- oleanolic acid, 3,4-dihydroxyphenylglycol and hydroxytyrosol, wherein the weight of the oleanolic acid with respect to the weight of the hydroxytyrosol is in the range from 10:1 to 1.1:1, preferably from 5:1 to 1.1:1, more preferably from 4:1 to 2:1.

As explained above, the product according to the present invention comprises one or more compounds of formula (I) and one or more compounds of formula (II) as previously defined. In one embodiment of the present invention, these two compounds of formula (I) and formula (II) form part of the same composition; preferably, the composition is a pharmaceutical composition that comprises the compound(s) of formula (I), the compound(s) of formula (II) and a pharmaceutically acceptable excipient.

Another aspect of the present invention relates to a pharmaceutical composition comprising the product according to the present invention which comprises a compound of formula (I) and a compound of formula (II), as defined above, and a pharmaceutically acceptable excipient, with the proviso that the composition comprises at a compound of formula (II) wherein $R^9$ and $R^{11}$ are H, and $R^{10}$ is OH (i.e. 3,4-dihydroxyphenylglycol).

In another aspect, the present invention relates to the use of a compound of formula (I) and a compound of formula (II), as defined above for the manufacture of a functional food.

The term "pharmaceutically acceptable excipient" refers to a vehicle, diluent, or adjuvant that is administered with the active ingredient. Such pharmaceutical excipients can be sterile liquids, such as water and oils, including those of petroleum, animal, vegetable, or synthetic origin, such as peanut oil, soybean oil, mineral oil, sesame oil, and similars. Water or saline aqueous solutions and aqueous dextrose and glycerol solutions, particularly for injectable solutions, are preferably used as vehicles. Suitable pharmaceutical vehicles are described in "Remington's Pharmaceutical Sciences" by E. W. Martin, 21st Edition, 2005.

Compounds of the invention may be administered by the oral, sublingual, parenteral, subcutaneous, intramuscular, intravenous, transdermal, intranasal, intraocular, and/or rectal routes.

The compounds of formula (I) and of formula (II) are commercially available and may be extracted from natural sources well known for those skilled in the art, as explained above.

Thus, in another aspect, the present invention relates to the product according to the present invention which comprises one or more compounds of formula (I) and a one or more compounds of formula (II) with the proviso that the product comprises a compound of formula (II) wherein $R^9$ and $R^{11}$ are H, and $R^{10}$ is OH, as defined above, for use as a medicament.

The present invention also provides the product according to the present invention which comprises one or more compounds of formula (I) and one or more compounds of formula (II) with the proviso that the product comprises a compound of formula (II) wherein $R^9$ and $R^{11}$ are H, and $R^{10}$ is OH, as defined above, in the manufacture of a medicament.

The present invention also provides the product as defined in the second aspect, for use in the treatment and/or prevention of a disease selected from the group consisting of Creutzfeldt-Jakob disease, Alzheimer's disease, Huntington's disease, Lewy body disease, Parkinson's disease, Pick's disease, amyotrophic lateral sclerosis, neurofibromatosis, epilepsy, brain injury, stroke, multiple sclerosis, ischemic hypoxia, spinal cord injury, loss of memory, mild cognitive impairment, dementia, and multiple infarct dementia.

The present invention also provides the use of the product as defined in the second aspect, for the manufacture of a medicament for the treatment and/or prevention of a disease selected from the group consisting of Creutzfeldt-Jakob disease, Alzheimer's disease, Huntington's disease, Lewy body disease, Parkinson's disease, Pick's disease, amyotrophic lateral sclerosis, neurofibromatosis, epilepsy, brain injury, stroke, multiple sclerosis, ischemic hypoxia, spinal cord injury, loss of memory, mild cognitive impairment, dementia, and multiple infarct dementia.

The present invention also provides a method of treatment and/or prevention of a subject in need thereof suffering or susceptible of suffering a disease selected from the group consisting of Creutzfeldt-Jakob disease, Alzheimer's disease, Huntington's disease, Lewy body disease, Parkinson's disease, Pick's disease, amyotrophic lateral sclerosis, neurofibromatosis, epilepsy, brain injury, stroke, multiple sclerosis, ischemic hypoxia, spinal cord injury, loss of memory, mild cognitive impairment, dementia, and multiple infarct dementia, which comprises the administration of a therapeutically effective amount of the product as defined in the second aspect.

The following examples represent specific embodiments of the present invention. They do not intend to limit in any way the scope of the invention defined in the present description.

EXAMPLES

Oleanolic acid, maslinic acid, ursolic acid, uvaol, erythrodiol, tyrosol, and 3,4-dihydroxyphenylglycol are commercially available from Sigma-Aldrich, hydroxytyrosol is commercially available from Extrasynthese (Genay Cedex, France), and verbascoside is commercially available from PhytoLab GmbH & Co. KGm (Vestenbergsgreuth, Germany).

Example 1

Pharmaceutical Compositions a) Capsule comprising the following ingredients:

| | |
|---|---|
| Total pentacyclic triterpenes of formula (I) | 100 mg |
| Oleanolic acid | 70 mg |
| Maslinic acid | 15 mg |
| Ursolic acid | 10 mg |
| Uvaol and erythrodiol | 5 mg |
| Total hydroxytyrosol derivatives of formula (II) | 26 mg |
| Hydroxytyrosol | 24 mg |
| 3,4-dihydroxyphenylglycol | 2 mg |
| Other components | |
| Tyrosol | 4 mg | b) Capsule comprising the following ingredients:

| | |
|---|---|
| Total pentacyclic triterpenes of formula (I) | 100 mg |
| Oleanolic acid | 100 mg |
| Total hydroxytyrosol derivatives of formula (II) | 62 mg |
| Verbascoside | 60 mg |
| 3,4-dihydroxyphenylglycol | 2 mg |

Example 2

Effects of Oleanolic Acid and Verbascoside Combination on Nitric Oxide Production by Lipopolysaccharide Plus Gamma-interferon Activated BV2 Microglia BV2 cells are a murine microglial-derived cell line widely used as in vitro model for the study of compounds that could modulate microglial mediated neuronal damage. When stimulated, BV2 microglia releases neurotoxic and neuroinflammatory factors such as tumor necrosis factor alpha (TNFα), interleukin 6 (IL6) or nitric oxide (NO).

The mouse microglial cell line BV-2 was purchased at the Istituto Nazionale per la Ricerca sul Cancro (1ST, Genova, Italy). BV-2 cells were cultured in RPMI-1640 medium (Gibco Invitrogen, Paisley, Scotland, UK) supplemented with 10% FBS and 0.1% penicillin-streptomycin (both from Gibco Invitrogen). Cells were maintained at 37° C. in a 5% $CO_2$ humidified atmosphere. BV-2 microglial cells were seeded at a density of $5 \times 10^4$ cells/mL. The following day, cells were treated with the compound of formula (I), the compound of formula (II) or the combination of both compounds, 30 minutes before stimulation with LPS 100 ng/mL and gamma-interferon (IFNγ) 50 pg/mL (both from Sigma-Aldrich, St. Louis, Mo., USA). Control wells contained the same final concentration of vehicle as the compound-containing wells. Culture supernatants were collected 24 h after LPS/IFNγ stimulation and stored at −20° C. until assayed for nitrites analysis.

Nitrite levels, direct indicators of NO production, were quantified by the Griess reaction. Briefly, 50 μL of culture medium was mixed in a 96-well plate with 25 μL of Griess reagent A (sulfanilamide, Sigma-Aldrich) and 25 μL of reagent B (N-1-naphthyl ethylene-diamine, Sigma-Aldrich). After color development (10 min at 23 to 25° C.), samples were measured at 540 nm on a microplate reader (BioTek ELX800, BioTek Instruments Inc., Vermont, USA). Nitrite concentration was determined from a sodium nitrite standard curve. Values of at least three independent wells from three experiments were calculated.

The compound of formula (I) was oleanolic acid (4.44 mg/L), the compound of formula (II) was verbascoside (3.12 mg/L), and the combination of the compound of formula (I) and the compound of formula (II) comprised oleanolic acid (4.44 mg/L) and verbascoside (3.12 mg/L). Stock solutions of the compounds (50 mM) were prepared in dimethyl sulfoxide (DMSO, Sigma-Aldrich). Solutions for cell treatment were prepared by diluting stock solutions in culture media immediately before being added to the cells (DMSO concentration: 0.5%). Controls contained the same final concentration of vehicle as the compound-containing wells. Three independent experiments were carried out.

The results showed a nitric oxide production decrease of 17.33% and 14.67% for LPS+IFNγ stimulated BV2 microglia treated with oleanolic acid and verbascoside, respectively. The reduction of NO production reached 39.33% for cells treated with the combination of oleanolic acid and verbascoside, higher than the sum of the effect of the single treatments (32.00%). Data is shown in FIG. 1 and Table 2.

Example 3

Effects of Maslinic Acid and Verbascoside Combination on Nitric Oxide Production by Lipopolysaccharide Plus Gamma-interferon Activated BV2 Microglia The procedures for this assay were as described above in Example 2, wherein the compound of formula (I) was maslinic acid (13.20 mg/L), the compound of formula (II) was verbascoside (3.12 mg/L), and the and the combination of the compound of formula (I) and the compound of formula (II) comprised maslinic acid (13.20 mg/L) and verbascoside (3.12 mg/L). Stock solutions of the compounds (50 mM) were prepared in dimethyl sulfoxide (DMSO, Sigma-Aldrich). Solutions for cell treatment were prepared by diluting stock solutions in culture media immediately before being added to the cells (DMSO concentration: 0.5%). Controls contained the same final concentration of vehicle as the compound-containing wells. Three independent experiments were performed.

Figure 2:
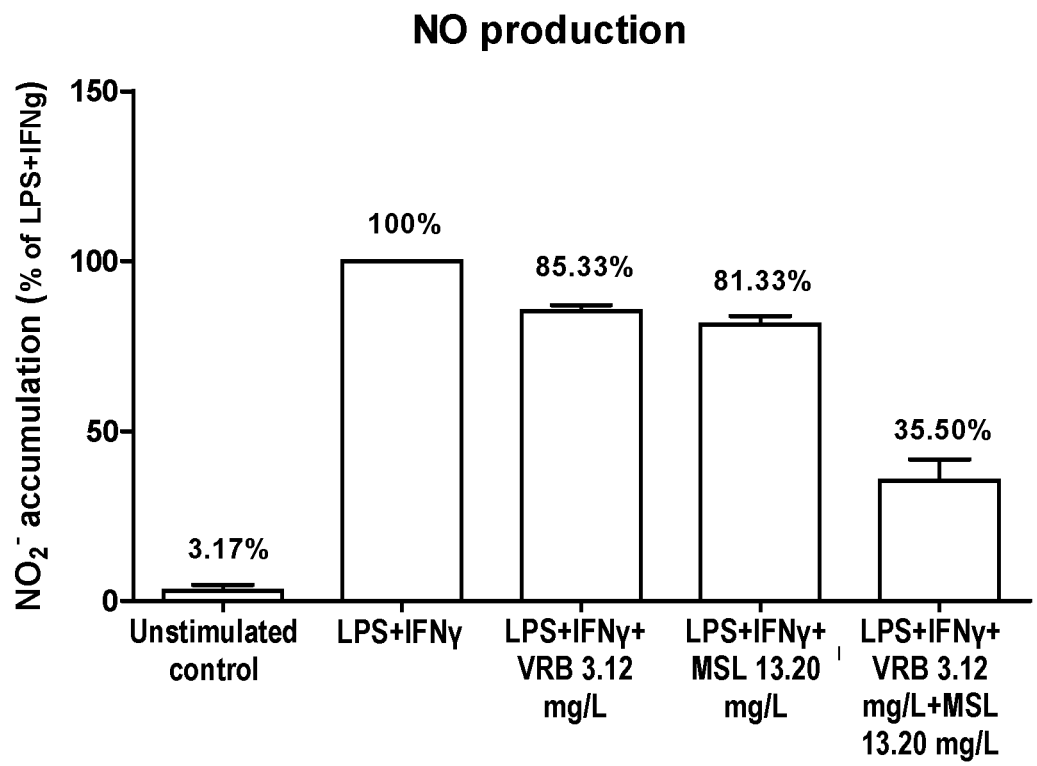
FIG. 2 shows NO production analysis in Lipopolysaccharide (LPS) plus gamma Interferon (IFNg) stimulated BV2 microglia treated with verbascoside 3.12 mg/L, maslinic acid (MSL) 13.20 mg/L or the combination of both. Results expressed as mean+SEM.

The results showed a reduction of 18.67% in NO production for the activated microglia treated with maslinic acid and a decrease of 14.67% in the cells treated with verbascoside. Cells treated with the combination of maslinic acid and verbascoside showed an inhibition of NO production of 64.50% when compared to the unstimulated condition. This value was clearly higher than the sum of the effect of both compounds tested separately (33.34%). Data is shown in FIG. 2 and Table 2.

Example 4

Effects of Hydroxytyrosol and Oleanolic Acid Combination on Motor Neuron Protection After Hydrogen Peroxide Mediated Insult NSC34 murine spinal cord motor neuron derived cell line was used for this assay. This neuronal cell line is a classical in vitro platform validated for the study of neuroprotective agents. They share a lot of common physiological features with spinal cord neurons such as glutamate sensibility, acetyl choline secretion upon stimulation, functional neurites or characteristic neuronal sensibility and protection mechanisms against neurotoxic agents.

Motoneuronal NSC-34 cells (Cedarlane, Burlington, Ontario, Canada) were cultured at 37° C. and 5% $CO_2$ in Dulbecco's modified Eagle's medium (DMEM) supplemented with 10% fetal bovine serum (FBS), 1% penicillin/streptomycin and 0.04 mM L-glutamine. All reagents were purchased at Gibco-Invitrogen. NSC34 cells were seeded at low density (30000 cel/mL) in appropriate tissue culture vessels, 24-well plates for toxicity assays. In the experiments, cells were pretreated for 2 h with the compound of formula (I) (oleanolic acid, 4.44 mg/L), the compound of formula (II) (hydroxytyrosol, 1.54 mg/L) or the combination of the compound of formula (I) (oleanolic acid, 4.44 mg/L) and the compound of formula (II) (hydroxytyrosol, 1.54 mg/L). Stock solutions of the compounds (50 mM) were prepared in dimethylsulfoxide (DMSO, Sigma-Aldrich). Solutions for cell treatment were prepared by diluting stock solutions in culture media immediately before being added to the cells (DMSO concentration: 0.5%). Controls contained the same final concentration of vehicle as the compound-containing wells. Hydrogen peroxide ($H_2O_2$) stock was a 30% solution in water (Aldrich). The medium was removed and replaced with a suitable volume of fresh DMEM plus FBS (Gibco). Small hydrogen peroxide aliquots were then added to a final concentration of 0.2 mM. Cells were then exposed for 30 min at 37° C. After this time the medium was removed and replaced with fresh one. The compounds were maintained in the medium for 24 hours. After this 24 hours cell viability was tested using the 3-[4,5-dimethylthiazol-2-yl]-2,5-diphenyltetrazolium bromide (MTT, Sigma) assay. After color development (15 min at 37° C.), samples were measured at 570-620 nm on a microplate reader (BioTek ELX800, BioTek Instruments Inc., Vermont, USA). Mean values of at least three independent wells from three experiments were calculated, and cell survival expressed as percent MU-positive signal compared with untreated control conditions. Treatments were also tested in undamaged control NSC34 and none of the conditions showed cell toxicity.

Figure 3:
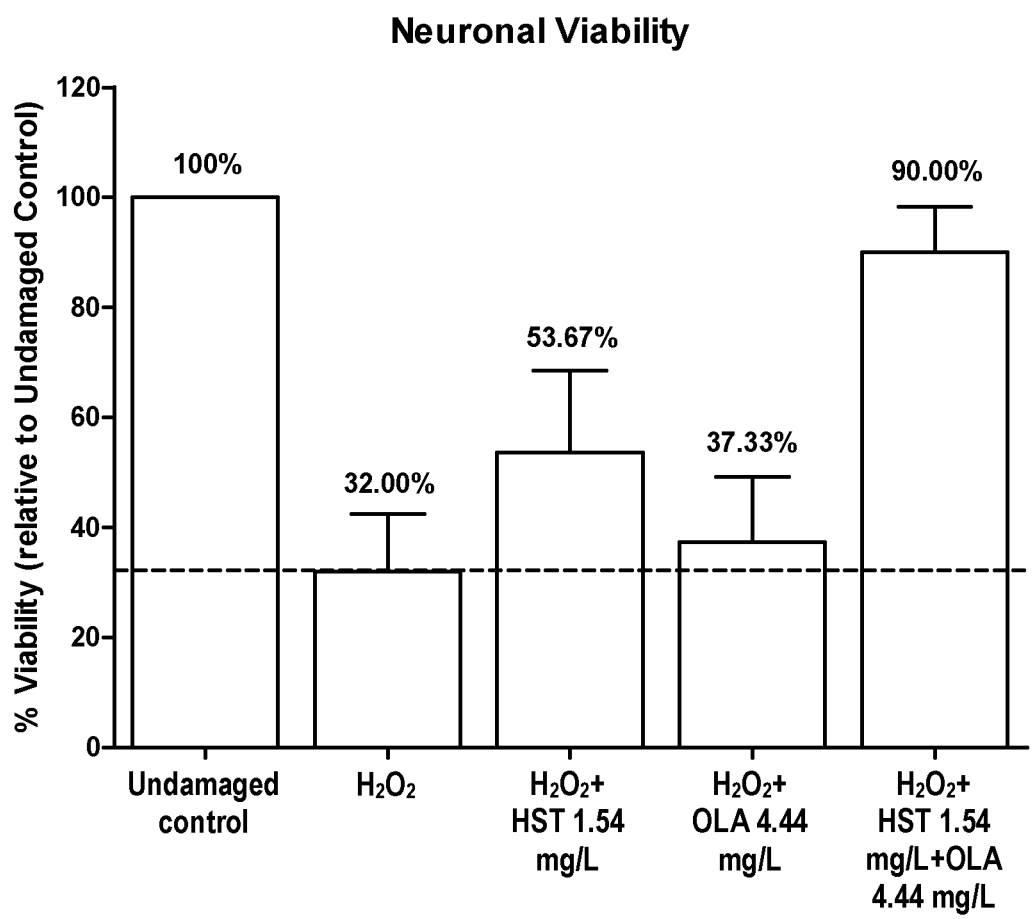
FIG. 3 shows the neuronal viability of NSC34 motor neurons damaged with hydrogen peroxide 0.2 mM ($H_2O_2$) and treated with hydroxytyrosol (HST) 1.54 mg/L, oleanolic acid 4.44 mg/L or the combination of both. Results expressed as mean+SEM.

When compared to untreated $H_2O_2$ insulted neurons, hydroxytyrosol treatment showed a neuronal viability increase of 21.67% whereas oleanolic acid increased viability by 5.33%. The combination of hydroxytyrosol and oleanolic acid resulted in an increase of NSC34 viability of 58.00%, clearly higher than the sum of the effect of single treatments (27.00%). Results are summarized at FIG. 3 and Table 2.

TABLE 2

Results of BV2 NO reduction and NSC34 survival by treatment with a compound of formula (I) (OLA: oleanolic acid; MSA: maslinic acid) and a compound of formula (II) (VRB: verbascoside; HST: hydroxytyrosol).

|  | Compound (I) | Compound (II) | Sum of the effect of single treatments | Combined treatment |
|---|---|---|---|---|
| Example 2 | OLA 4.44 mg/L | VRB 3.12 mg/L | OLA 4.44 mg/L + VRB 3.12 mg/L | OLA 4.44 mg/L + VRB 3.12 mg/L |
| BV2 NO reduction (vs. LPS + IFNγ) | 17.33% | 14.67% | 32.00% | 37.33% |
| Example 3 | MSA 13.20 mg/L | VRB 3.12 mg/L | MSA 13.20 mg/L + VRB 3.12 mg/L | MSA 13.20 mg/L + VRB 3.12 mg/L |
| BV2 NO reduction (vs. LPS + IFNγ) | 18.67% | 14.67% | 33.34% | 64.50% |
| Example 4 | OLA 4.44 mg/L | HST 1.54 mg/L | OLA 4.44 mg/L + HST 1.54 mg/L | OLA 4.44 mg/L + HST 1.54 mg/L |
| NSC34 survival increase (vs. H$_2$O$_2$) | 5.33% | 21.67% | 27.00% | 58.00% |

The invention claimed is:

1. A composition comprising:
   a) 1, 2, 3, 4, or 5 compounds selected from the group consisting of oleanolic acid, maslinic acid, ursolic acid, erythtodiol and uvaol; or pharmaceutically acceptable salts thereof; and
   b) 1, 2 or 3 compounds selected from the group consisting of hydroxytyrosol, verbascoside, and 3,4-dihydroxyphenylglycol; or pharmaceutically acceptable salts thereof;
   wherein the weight of the compounds of (a) with respect to the weight of the compounds of (b) is in the range from 10:1 to 1:1;
   with the provisos that:
      the product comprises 3,4-dihydroxyphenylglycol,
      when the product comprises oleanolic acid and hydroxytyrosol, then the weight of oleanolic acid is at least 3 times the weight of hydroxytyrosol; and
      when the product comprises hydroxytyrosol, maslinic acid and oleanolic acid in a weight ratio maslinic acid/oleanolic acid greater than 1, then the weight of maslinic acid is at least 10 times the weight of hydroxytyrosol.

2. The composition according to claim 1, comprising 1 or 2 compounds of (a), wherein the 1 or 2 compounds of (a) is/are selected from the group consisting of oleanolic acid and maslinic acid.

3. The composition according to claim 1, wherein the 1, 2 or 3 compounds of (b) is/are selected from the group consisting of hydroxytyrosol, verbascoside, and 3,4-dihydroxyphenylglycol.

4. The composition according to claim 1 comprising a combination of compounds of (a) and compounds of (b) selected from the group consisting of:
   oleanolic acid, 3,4-dihydroxyphenylglycol and verbascoside,
   maslinic acid, 3,4-dihydroxyphenylglycol and verbascoside, and
   oleanolic acid, 3,4-dihydroxyphenylglycol and hydroxytyrosol.

5. A pharmaceutical composition comprising the composition of claim 1 and a pharmaceutically acceptable excipient.

* * * * *